(12) United States Patent
Yamamoto et al.

(10) Patent No.: US 7,875,255 B2
(45) Date of Patent: Jan. 25, 2011

(54) NANOPARTICLES COMPRISING CALCIUM PHOSPHATE AND ETHYLENE IMINE COMPOSITIONS AND METHODS OF PRODUCTION THEREOF

(75) Inventors: Akira Yamamoto, Tokyo (JP); Yusuke Iimori, Tokyo (JP); Mae Koyama, Tokyo (JP)

(73) Assignee: Hoya Corporation, Tokyo (JP)

( * ) Notice: Subject to any disclaimer, the term of this patent is extended or adjusted under 35 U.S.C. 154(b) by 979 days.

(21) Appl. No.: 11/531,909

(22) Filed: Sep. 14, 2006

(65) Prior Publication Data

US 2010/0311902 A1 Dec. 9, 2010

(30) Foreign Application Priority Data

Sep. 16, 2005 (JP) .............................. 2005-271101

(51) Int. Cl.
*C01B 15/16* (2006.01)
*C01B 25/26* (2006.01)
*C12N 15/00* (2006.01)
*A61K 48/00* (2006.01)

(52) U.S. Cl. ........................ 423/308; 977/773; 435/455; 435/320.1; 514/44 R

(58) Field of Classification Search ........................ None
See application file for complete search history.

(56) References Cited

U.S. PATENT DOCUMENTS

| 6,586,524 | B2* | 7/2003 | Sagara ..................... 525/54.11 |
| 7,358,223 | B2* | 4/2008 | Zhao et al. ..................... 514/1 |
| 7,776,600 | B2* | 8/2010 | Kumta et al. ................. 435/455 |
| 2003/0166601 | A1* | 9/2003 | Woodle et al. ................. 514/44 |
| 2005/0176897 | A1 | 8/2005 | Kanzaki et al. |
| 2007/0048383 | A1* | 3/2007 | Helmus ..................... 424/489 |
| 2007/0054337 | A1* | 3/2007 | Ferning et al. ............. 435/7.92 |
| 2007/0072815 | A1* | 3/2007 | Kmiec et al. .................. 514/44 |
| 2009/0155320 | A1* | 6/2009 | Rudin et al. ................. 424/401 |

FOREIGN PATENT DOCUMENTS

JP 2005-248144 9/2005

OTHER PUBLICATIONS

Kim, et al. (2004) Japanese Journal of Applied Physics, 43(11A): 7434-38.*
U.S. Appl. No. 11/430,989, filed May 10, 2006, and entitled "Nanoparticles of Calcium Phsophate Compound, Dispersion Liquid Thereof and Method of Production Thereof".
U.S. Appl. No. 11/428,418, filed Jul. 3, 2006, and entitled "Highly Dispersible Inorganic Compound Nanoparicels and Method of Production Thereof".

* cited by examiner

*Primary Examiner*—Robert M Kelly
(74) *Attorney, Agent, or Firm*—Greenblum & Bernstein, P.L.C.

(57) ABSTRACT

Highly dispersible inorganic compound nanoparticles modified by functional molecules include the functional molecules; a high molecular nitrogen compound having at least two amino groups selected from primary amino groups, secondary amino groups and tertiary amino groups; and inorganic compound nanoparticles bonded to at least one amino group of the at least two amino groups. The high molecular nitrogen compound is modified by the functional molecules, and the inorganic compound nanoparticles are covered with the high molecular nitrogen compound modified by the functional molecules.

10 Claims, 12 Drawing Sheets

Polyethyleneimine (PEI)

○ ● : Ethyleneimine Monomer 100 nm

NANOPARTICLES COMPRISING CALCIUM PHOSPHATE AND ETHYLENE IMINE COMPOSITIONS AND METHODS OF PRODUCTION THEREOF

BACKGROUND OF THE INVENTION

1. Field of the Invention

The present invention relates to highly dispersible inorganic compound nanoparticles having good dispersibility which bond to various functional molecules, and a method of production thereof.

2. Description of the Prior Art

Recently, nanotechnology research has been widely carried out and atomization (nanoparticle-formation) processes of many kinds of substances used as materials are being researched in various industrial fields. Because such nanoparticle-formed materials show an improvement of flowability, an increase in surface area and an enhancement of reactivity on the surface, by applying such a change of physical properties, an improvement in density at the time of compression molding, an increase in adsorption capacity, an improvement of a function as a chemical reaction catalyst and the productivity of a composite with other materials can be achieved easily. The functionalization of nanoparticles to other materials by mixing or forming a composite with other materials is commonly applied in the fields of coatings, surface modification materials, cosmetics, high refraction index glasses, ceramics, strong magnetic materials and semiconductors materials, etc.

Accordingly, nanoparticle formation of substances has become extremely important technology, and there are prospects for application thereof to the fields of chemistry, biochemistry, molecular biology and medical science. Recently, experiments have been made with very small particles being combined with a labeled compound to identify, detect, quantify and visualize a specific molecular structure. Calcium phosphate compound and silica which have very excellent stability at the time of preservation and are harmless to a living body are used as particles. If such particles can be used in nanoparticle form, it is possible to combine them with much more labeled compound molecules so that a large improvement in sensitivity is achievable.

For example, a protein is impossible to be visually observed because they are transparent in a solution except special examples such as some colored proteins. Additionally it is difficult to detect only a specific protein in the state where many substances are intermingled. Therefore some solution procedures such as binding the protein with pigment molecules having specific optical characteristics, labeling with a radioisotope, or binding other enzymes have been developed, and the detection and quantification of the target protein in the mixture are carried out. These solution procedures are used abundantly for the purpose of identifying, detecting and quantifying not only the protein but the target substance in a solution series or an internal environment of a live body in which DNA, RNA and sugars, etc., are intermingled.

In the case where these labeled molecules are antigens, antibody proteins, sugars, receptors, ligands, nucleotides, etc., which recognize a specific molecular structure, these substances are used for identifying, detecting, quantifying and visualizing a certain molecular structure. In the case where the labeled substance is detected and quantified spectroscopically, labeling by a radioisotope was performed in the past, however, recently coloring matters are often utilized (color labeling method). When the concentration of a labeled compound is low, labeling with an enzyme, etc., is performed to carry out a converting reaction of the substrate with a small quantity of enzyme over a long period of time to make detection possible (enzyme labeling method).

Furthermore, a labeling method with very small particles, which is a recent trend, has attracted considerable attention due to a labeling compound such as a coloring matter being able to be accumulated in a particle at a high concentration using very small particles.

However, because inorganic compound nanoparticles have a strong aggregation property in a solution, when the surfaces of the particles are covered with the labeled compounds, the aggregation property thereof is strengthened, so that the particles become bulky causing deterioration of sensitivity.

SUMMARY OF THE INVENTION

The present invention provides highly dispersible inorganic nanoparticles with a low aggregation property, even though the nanoparticles are covered with labeled compounds, and provides an efficient method of production thereof.

The present invention has been devised based on the finding that polyamine compound shows strong adsorptivity for inorganic compound particles and can improve the dispersibility of inorganic compound particles.

According to an aspect of the present invention, highly dispersible inorganic compound nanoparticles modified by functional molecules are provided, including the functional molecules; a high molecular nitrogen compound having at least two amino groups selected from primary amino groups, secondary amino groups and tertiary amino groups; and inorganic compound nanoparticles bonded to at least one amino group of the at least two amino groups. The high molecular nitrogen compound is modified by the functional molecules, and the inorganic compound nanoparticles are covered with the high molecular nitrogen compound modified by the functional molecules.

It is desirable for the number average molecular weight of the high molecular nitrogen compound to be in the range from 800 to 100,000.

It is desirable for the high molecular nitrogen compound to include, in the molecules thereof, primary amino groups, secondary amino groups, and tertiary amino groups in a repeating unit.

It is desirable for the high molecular nitrogen compound to include one of a straight-chain, a branched-chain and a cyclic polyamine compound or a mixture thereof.

It is desirable for the polyamine compound to include polyethylene imine.

It is desirable for the inorganic compound to include one of calcium phosphate compound and metal oxide.

It is desirable for the calcium phosphate compound to include hydroxyapatite.

It is desirable for the metal oxide to include one of alumina, silica, magnesium oxide, andiron oxide.

It is desirable for the functional molecules to include organic coloring matters, inorganic coloring matters, fluorochrome or chemical identifiable molecules having chemiluminescent atomic groups.

It is desirable for the functional molecules to include molecules having a specific functionality and derived from a living body such as enzyme, antibody, cell-irritating factor, collagen, virus envelope protein, cell bonding ligand, colored protein, fluoro-protein, oligonucleotide, DNA, RNA, metal-storage protein, monosaccharides, oligosaccharides or polysaccharides.

In an embodiment, a method of production for highly dispersible inorganic compound nanoparticles is provided, including reacting functional molecules with a high molecular nitrogen compound having at least two amino groups selected from primary amino groups, secondary amino groups and tertiary amino groups; mixing a solution containing the high molecular nitrogen compound modified by the functional molecules formed and inorganic compound nanoparticles; centrifuging the mixture after ultrasonicating; collecting a supernatant of the mixture; and drying the supernatant.

It is desirable for the number average molecular weight of the high molecular nitrogen compound to be in a range from 800 to 100,000.

It is desirable for the high molecular nitrogen compound to include, in the molecular thereof, primary amino groups, secondary amino groups and tertiary amino groups in a repeating unit.

It is desirable for the high molecular nitrogen compound to include one of a straight-chain, a branched-chain and a cyclic polyamine compound or mixture thereof.

It is desirable for the polyamine compound to include polyethylene imine.

It is desirable for the inorganic compound to include one of calcium phosphate compound and metal oxide.

It is desirable for the calcium phosphate compound to be hydroxyapatite.

It is desirable for the metal oxide to include alumina, silica, magnesium oxide, and iron oxide.

It is desirable for a solvent of the high molecular nitrogen compound to be one of water and an organic solvent.

It is desirable for the functional molecules to include chemical identifiable molecules having organic coloring matters, inorganic coloring matters, fluorochrome or chemiluminescent atomic groups.

It is desirable for the functional molecules to include molecules having a specific function and derived from a living body such as enzyme, antibody, cell-irritating factor, collagen, virus envelope protein, cell bonding ligand, colored protein, fluoro-protein, oligonucleotide, DNA, RNA, metal-storage protein, monosaccharides, oligosaccharides or polysaccharides.

When the highly dispersible inorganic compound nanoparticles according to the present invention are produced, the solvent of the high molecular nitrogen compound can be water or an organic solvent, such as alcohol (e.g., ethanol, isopropanol, etc.).

According to the present invention, it is possible for the surfaces of inorganic compound nanoparticles to be modified to provide highly dispersible inorganic compound nanoparticles that have good dispersibility in water solution and are covered with various functional molecules. Furthermore, because inorganic compound nanoparticles according to the present invention are covered with functional molecules such as various labeling compounds, various applications in the chemical, biochemical and medical fields are expected.

The present disclosure relates to subject matter contained in Japanese Patent Application No. 2005-271101 (filed on Sep. 16, 2005) which is expressly incorporated herein in its entirety.

BRIEF DESCRIPTION OF THE DRAWINGS

The present invention will be discussed below in detail with reference to the accompanying drawings, in which.

DESCRIPTION OF THE PREFERRED EMBODIMENTS

The highly dispersible inorganic compound nanoparticles according to the present invention are covered with a high molecular nitrogen compound which is modified by functional molecules which are obtained by reacting functional molecules and a high molecular nitrogen compound.

Useful functional molecules are not restricted to a specific substance, and include organic coloring matters, inorganic coloring matters (pigments), fluorochromes or chemical identifiable molecules having chemiluminescent atomic groups or molecules having a specific function and derived from a living body such as enzyme, antibody, cell-irritating factor, collagen, virus envelope protein, cell bonding ligand, colored protein, fluoro-protein, oligonucleotide, DNA, RNA, metal-storage protein, monosaccharides, oligosaccharides or polysaccharides.

Additionally, the high molecular nitrogen compound may have at least two amino groups selected from primary amino groups, secondary amino groups and tertiary amino groups in the molecule. For example polyamine compound can be used. The polyamine compound can be a straight-chain, branched-chain or cyclic compound, and if a plurality of the primary amino groups, secondary amino groups and tertiary amino groups exist in a repeating unit structure in a molecule, the bonding sites for the inorganic compound nanoparticles desirably increase.

Figure 1:
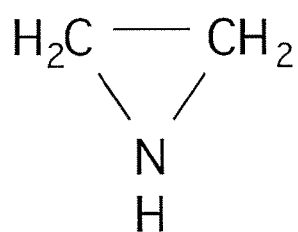
FIG. 1 shows a molecular formula of ethyleneimine monomer.
Figure 2:
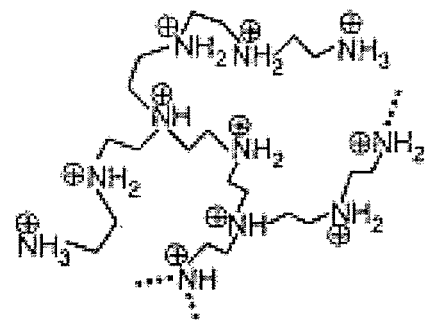
FIG. 2 shows a molecular structure of polyethylene imine.
Figure 3:
FIG. 3 shows a molecular structure of polyethylene imine consisting only of primary and secondary amino groups.
Figure 4:
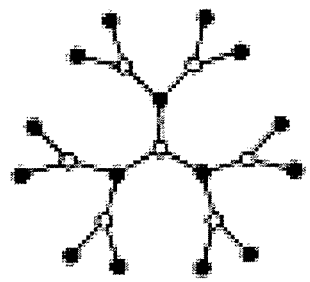
FIG. 4 shows a molecular structure of polyethylene imine consisting only of primary and tertiary amino groups.

Furthermore, polyethylene imine compound or polylysine, etc., can be used as the polyamine compound and polyethylene imine (FIG. 2) is particularly suitable. Polyethylene imine is a polymer of ethylene imine (FIG. 1), and the molecular structure is different depending on the amino group concerned with the polymerization. FIG. 3 is a schematic diagram showing a molecular structure of polyethylene imine consisting of only primary amino groups and secondary amino groups, and FIG. 4 is a schematic diagram showing a molecular structure of polyethylene imine consisting of only primary amino groups and tertiary amino groups.

It is desirable for the number average molecular weight of polyamine compound (high molecular nitrogen compound) is 800 to 100,000. A number average molecular weight of less than 800 may cause difficulty for the polyamine compound to cover the inorganic compound nanoparticles completely, and therefore, being difficult to attain good dispersibility because the particles are bonded to each other. Furthermore, the number average molecular weight of above 100,000 may prevent good dispersibility from being attained because the polyamine compounds are bonded each other to form large agglomerates.

Highly dispersible inorganic compound nanoparticles according to the present invention are covered with high molecular nitrogen compounds by bonding the inorganic compound nanoparticles at a solid acidity (electron pair receptor) to at least one of amino groups in the high molecular nitrogen compound. Calcium phosphate compound or metal oxide can be used as an inorganic compound.

A calcium phosphate compound having a Ca/P ratio of 1.0 to 2.0 may be used as the calcium phosphate compound, and typical examples thereof include various apatites such as hydroxyapatite and fluoroapatite, calcium primary phosphate, calcium secondary phosphate, and tricalcium phosphate, and tetracalcium phosphate. These calcium phosphate compounds may be used alone or as a mixture thereof.

Furthermore aluminium oxide, silicon dioxide, magnesium oxide, titanium oxide, iron oxide (hematite) are examples of metal oxides which can be used.

It is desirable for nanoparticles of an inorganic compound used in the present invention to have an average particle size of 2 nm to 1,000 nm (1 μm). It is difficult to produce enough nanoparticles with an average particle size of less than 2 nm for industrial use. On the other hand, when the size is above 1,000 nm, they do not agglomerate too much, and their dispersibility is comparatively good by themselves.

The inorganic compound nanoparticles used as a starting material in the present invention can be finely divided particles adhered to nanoparticles or nanoparticle agglomerates, prepared according to a desired method.

For example, the method of production of the calcium phosphate compound nanoparticles developed by the present inventors is described as follows. Namely, the calcium phosphate compound nanoparticles are prepared by thermal treating a calcium phosphate compound, dispersing the obtained calcium phosphate compound particles in an organic solvent, crushing the particles, centrifuging the obtained calcium phosphate compound dispersion liquid, collecting the supernatant and, if necessary, drying the supernatant. In this method, the thermal treated calcium phosphate compound particles can be treated in a ball mill before crushing.

It is desirable for the calcium phosphate compound, used for the above-mentioned method as a raw material, to be synthesized by a known process, dried before heat treating, and granulated if necessary. Granulation can be performed by a known process, however, it is desirable for a porous body to be made at a volume ratio of more than 70% with a spray-dry process.

In the above method, calcium phosphate compound is first thermally treated using a known method to provide a thermal history. The heating temperature is not restricted, however, it is desirable for the heating process to be performed at a temperature of about 400° C. to 1050 r. When the temperature of the heating process is lower than 400° C., a sufficient strength can not be obtained to reduce the use strength, and if the temperature is higher than 1050° C., a part or all of the particles sinter, reducing the yield of the nanoparticles.

After thermal treating, the particles are dispersed in an organic solvent by a crush treatment such as, for example, ultrasonication or homogenizing treatment, using a shaker or using a mortar. It is desirable for a polar organic solvent, for example, alcohol (such as ethanol, isopropanol), ether (such as 2-ethoxyethanol), acetonitrile, tetrahydrofuran and dimethyl sulphoxide to be used as an organic solvent.

Before the crushing process, calcium phosphate compound particles can be treated in a ball mill apparatus. The ball mill apparatus normally uses balls (media) that crush the sample material with grinding movement. However, the treatment is performed without using balls so as to obtain a high yield of spherical nanoparticles (an aspect ratio thereof being almost 1). It is desirable that this treatment is carried out under dry conditions (hereinafter referred to as a dry mill treatment) without using an organic solvent (namely, only calcium phosphate compound is set in the pot).

The calcium phosphate compound dispersion liquid obtained is centrifuged to fractionate a supernatant containing calcium phosphate compound nanoparticles dispersed in an organic solvent layer and a deposit consisting of particles having a larger particle size. Thereafter, the organic solvent in the supernatant is evaporated to obtain calcium phosphate compound nanoparticles.

Highly dispersible inorganic compound nanoparticles according to the present invention can be prepared by reacting functional molecules with the high molecular nitrogen compound having at least two amino groups selected from primary amino groups, secondary amino groups and tertiary amino groups, mixing the prepared solution containing the functional molecule-modified high molecular nitrogen compound and inorganic compound nanoparticles, ultrasonicating the mixture, centrifuging, and then collecting the supernatant and drying the supernatant.

Since the dispersibility of highly dispersible inorganic compound nanoparticles does not show an apparent difference depending on the kind of solvent of the reactive solution of the functional molecules and the high molecular nitrogen compound used in the present invention, it is possible to use any desirable solvent which can dissolve a high molecular nitrogen compound to be used as a solvent. Water or alcohols (for example, ethanol, iospropanol) can be used as a solvent, if the high molecular nitrogen compound is, for example, PEI.

In addition, the concentration of the functional molecules used can be decided appropriately depending on the purpose of the use.

Furthermore, the concentration of the high molecular nitrogen compound used is dependent on the sort, quantity and the surface area, etc., of the inorganic compound nanoparticles to be covered, and cannot be decided at just one point. However, if the concentration of the high molecular nitrogen compound is too low, the high molecular nitrogen compound will bond to the particles but cannot cover the particles completely, so the agglomeration occurs as a result of the particles bonding to each other. If the concentration of the high molecular nitrogen compound is too high, the high molecular nitrogen compound will bond to the particles, the nitrogen compounds also bond to each other, so that large micelles are produced, resulting in agglomeration occurring. Therefore it is desirable for the concentration of the high molecular nitrogen compound to be selected properly each time in depending on a sort, quantity and surface area of the inorganic compound nanoparticles to be covered.

In addition, suitable covering amounts of the high molecular nitrogen compound for the inorganic compound nanoparticles vary depending on the sort and surface area of the inorganic compound nanoparticles to be covered and the sort and molecular weight of the high molecular nitrogen compound to be used, and cannot be decided at just one point. However, for example, when hydroxyapatite nanoparticles are covered with polyethylene imine (PEI), it is desirable for the weight ratio of PEI/nanoparticles to be 1 to 100 mg/g, and more desirable to be 10 to 50 mg/g.

When magnesium oxide nanoparticles are covered with PEI, it is desirable for the weight ratio of PEI/nanoparticles to be 0.1 to 10 mg/g, especially desirable to be 1 mg/g. Furthermore when nanoparticles of aluminum oxide, silicon dioxide, titanium oxide or iron oxide(hematite) are covered with PEI, it is desirable for the weight ratio of PEI/nanoparticles to be 1 to 100 mg/g, and particularly desirable to be 50 mg/g.

Since inorganic compound nanoparticles are easy to agglomerate, they are ultrasonicated after mixing with high molecular nitrogen compound solution. Ultrasonic at ion makes it possible for inorganic compound nanoparticles to be dispersed mechanically and simultaneously to be covered uniformly and efficiently with the high molecular nitrogen compound.

When the method of production of calcium phosphate compound nanoparticles above mentioned is performed, particles which sustained thermal treatment can be mixed with high molecular nitrogen compound solution before crushing (ultrasonication).

By centrifuging the high molecular nitrogen compound covered inorganic compound nanoparticles obtained in such a way, collecting, and drying the supernatant containing these covered inorganic compound nanoparticles, the inorganic compound nanoparticles covered with high molecular nitrogen compound are attained.

When ultrasonicating, the concentration of inorganic compound nanoparticles solution is adjusted higher in order to improve the dispersibility and covering effect. Hence before performing the above-mentioned centrifuging, distilled water may be added to dilute the solution if necessary.

The present invention will be explained in detail based on the following examples, however, the present invention is not restricted thereto.

The inorganic compound nanoparticles covered with high molecular nitrogen compounds obtained in the following examples were evaluated according to the following processes.

(A) Particle Shape

The shapes of the covered nanoparticles were observed using a transmission electron microscope (TEM). H-7600 made by HITACHI Ltd., JAPAN, was used as the transmission electron microscope.

(B) Fluorescence Microscopic Photograph

The nanoparticles covered with the functional molecule-modified polyethylene imine (PEI) and the nanoparticles covered with PEI were observed using a fluorescence microscope. These observations were performed with an upright microscope DMR made by LEICA, Ltd., and the exciter filter BP480/40 and the absorption filter BP600/40 were used. The proper amounts of nanoparticles above-mentioned were dripped on a slide glass and the glass was photographed using an oil immersion lens.

(C) Particle Size Distribution

The particle size distribution was measured for the covered nanoparticles dispersion liquid. The measurement of the particle size distribution was performed with a Submicron Particle Analyzer N5, manufactured by Beckmann-Coulter Ltd., JAPAN, using a dynamic scattering method. The results measured 3 times were shown in each of the following examples and comparative examples. The vertical axis in each distribution diagram represents a peak strength(%). In the scale of the vertical axis, 20, 40, 60, 80 and 100 are inscribed sequentially from the bottom. The horizontal axis shows the particle diameter (nm) of a nanoparticle represented as a logarithm. In the scale of the horizontal axis, 2, 4, 8, 16, 32, 64, 128, 256, 512, 1024 and 2048 are inscribed sequentially from the left. In the graphs, the blue line shows the measurement result at first time, red line shows the result at second time and green line shows the result at third time.

(D) Fluorescence Strength

Generally, fluorescence is the light that is a part of energy emitted by a fluorescent substance when the energy thereof shifts from a stable ground state to an unstable exited state, and returns to the stable ground state again by absorbing the optical energy of a specific wavelength corresponding to each substance. In the case of Fluorescein-4-isothiocyanate (FITC), it absorbs the light of 495 nm weave length, and emits fluorescence of 520 nm. Accordingly, the existence of FITC can be checked by the absorption spectrum near 495 nm.

Accordingly, the absorption spectrum was measured for the FITC modified PEI covered nanoparticles dispersion liquid. For measuring the absorption spectrum, an ultraviolet visible spectrophotometer BioSpec-1600 made by SIMAZU SEISAKUSHO Ltd. was used.

Example 1

Coating and Optical Characteristics of FITC Modified PEI Hydroxyapatite Nanoparticles (HA Nanoparticles (1) Preparation of FITC Modified PEI Solution In order to prepare the FITC modified PEI solution, 5.4 mg of FITC dissolved in 100 ml of distilled water and 100 mg of PEI (P-70 made by WAKO-JUNYAKU, Ltd.; an average molecular weight 70,000) were mixed, and then diluted with distilled water so as to obtain 1.75 mg/ml concentration of polyethylene imine.

(2) Preparation of Hydroxyapatite Nanoparticles

Phosphate water solution and calcium salt water solution were mixed to provide a slurry containing hydroxyapatite. The slurry containing hydroxyapatite was dried with spray-dry equipment at 200° C., granulated, and thereafter classified into a mean particle size of 10 μm. The obtained hydroxyapatite particles were inserted into an electric oven and thermally treated. The thermal treatment was performed by rising the temperature at the rate of 50° C./hr to 850° C. and then maintaining the temperature at 850° C. for four hours to obtain hydroxyapatite particles (HA particles).

(3) Preparation of Hydroxyapatite Nanoparticles Covered with FITC Modified PEI 1.0 g of the HA particles prepared according to above method (2) were placed in a 45 ml pot (made from zirconia) and were dry mill treated with a Planetary ball mill (manufactured by Fritsch Ltd.: P-7) at a milling rotation of 800 rpm for 3 hours. In addition, dry milling was conducted without using media in the pot in a Planetary Ball mill apparatus. HA particles were collected after dry milling to provide dry milled HA particles.

10 g of dry milled HA particles were added to 30 ml of FITC modified PEI solution prepared according to above method (1) so as to disperse; the resulting HA particles were crushed by ultrasonication with an ultrasonic generator (manufactured by TAITEC Ltd., VP-30S)(out put 180 W, 5 min.), and the surface of HA particles were covered with FITC modified PEI. Thereafter, distilled water was added to make the total quantity to 100 ml and centrifuging was conducted at 4100×g for 5 minutes. The supernatant obtained after centrifuging, namely the FITC modified PEI covered HA nanoparticles dispersion liquid was collected.

The results of various analysis of the FITC modified PEI covered HA nanoparticles prepared in this example are shown as follows.

(A) Particle Shape

Figure 5:
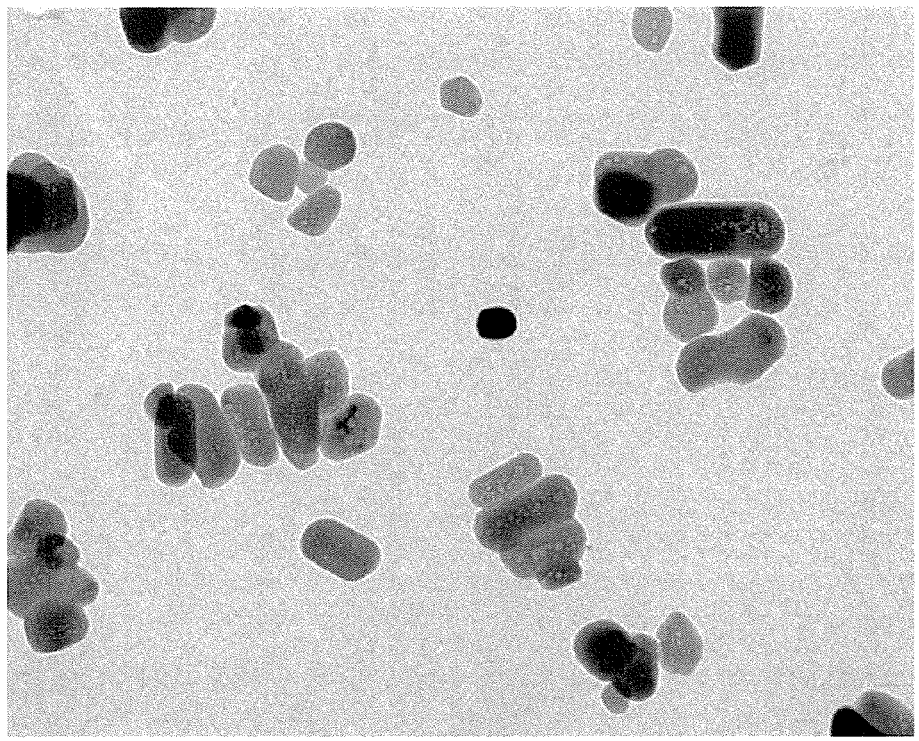
FIG. 5 is a transmission electron microphotograph of hydroxyapatite nanoparticles with FIPC modified PEI coatings prepared in Example 1.

FIG. 5 is a transmission electron microphotograph of the FITC modified PEI covered HA nanoparticles. As shown in this TEM photograph, the HA nanoparticles were spherical or oval-spherical with a size of 30 nm to 175 nm, and the particles were monodispersed, or dispersed with several particles gathered together.

(B) Fluorescence Microphotograph

Figure 6:
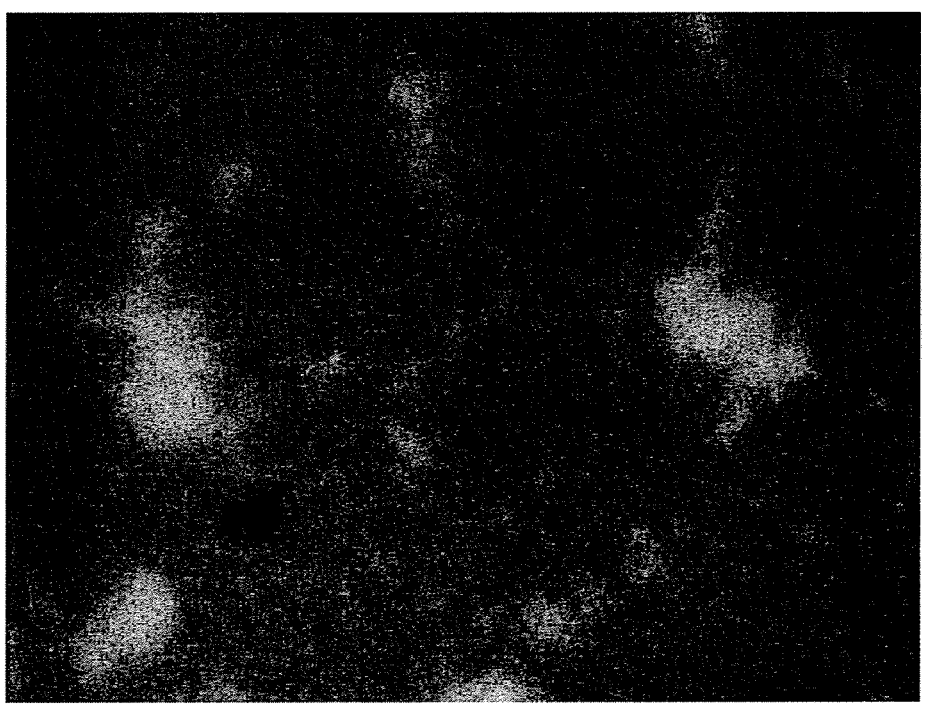
FIG. 6 is a fluorescence microphotograph of hydroxyapatite nanoparticles with FIPC modified PEI coatings prepared in Example 1.

FIG. 6 is a fluorescence microphotograph that is photographed at a magnification of 1,000 times. The white parts show the fluorescence of FITC. Since the particles are very fine, they appear dim overall. The whitest parts are the parts where the particles agglomerate.

(C) Particle Size Distribution

Figure 7:
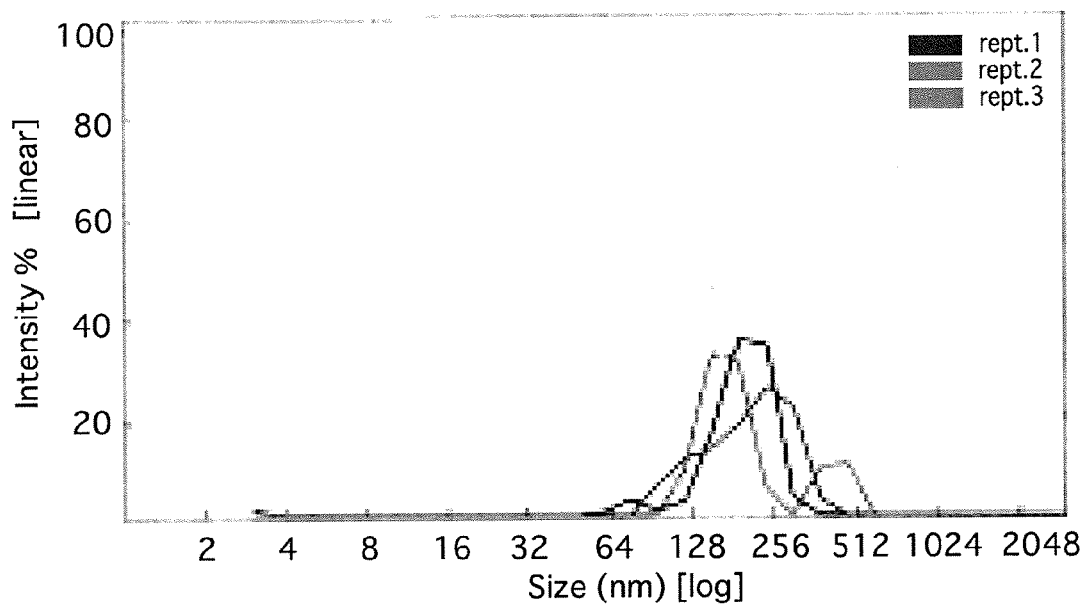
FIG. 7 is a graph of a particle size distribution of hydroxyapatite nanoparticles with FIPC modified PEI coatings prepared in Example 1.

FIG. 7 is a graph of a particle size distribution of the FITC modified PEI covered HA nanoparticle dispersion liquid by dynamic scattering method, the average particle size of the nanoparticles in the dispersion liquid being about 192 nm.

Example 2

Coating and Optical Characteristics of FITC Modified PEI Alumina Nanoparticles

Alumina nanoparticles were coated with FITC modified PEI with the following method.

1 g of alumina nanoparticles (made by C.I. KASEI Ltd., JAPAN, NanoTek Powder; $Al_2O_3$) was added to 30 ml of the FITC modified PEI solution prepared by the process similar to Example 1 to disperse, and the alumina nanoparticles were covered with FITC modified PEI by ultrasonicating with an ultrasonic generator (TAITEC Ltd.; VP-30S) (output 180 W for 1 minute). Thereafter, distilled water was added to make a total amount of 100 ml, and centrifuged at 4100×g for 5 minutes. The supernatant obtained after centrifuging, namely, the FITC modified PEI covered alumina nanoparticles dispersion liquid, was collected.

The results of various analysis of the FITC modified PEI covered alumina nanoparticles obtained in this example are as follows.

(A) Particle Shape

Figure 8:
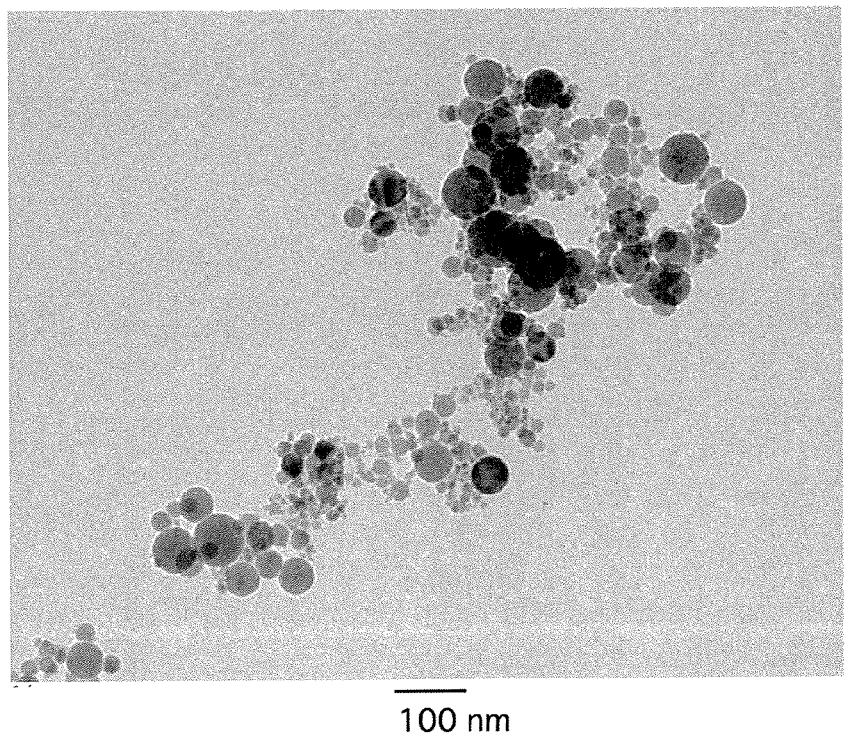
FIG. 8 is a transmission electron microphotograph of alumina nanoparticles with FIPC modified PEI coatings prepared in Example 2.

FIG. 8 is a transmission electron microphotograph of the FITC modified PEI covered alumina nanoparticles. As shown in this TEM photograph, the nanoparticles were spherical with a size of 5 nm to 150 nm and they were dispersed with several or more particles gathered together.

(B) Fluorescence Microphotograph

Figure 9:
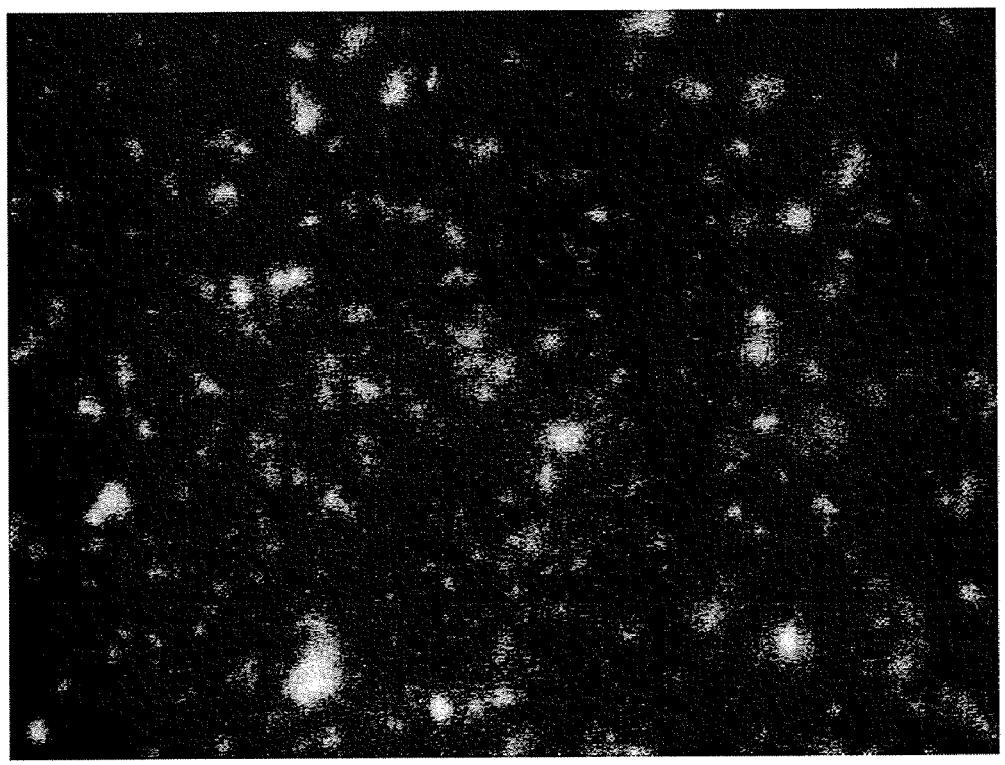
FIG. 9 is a fluorescence microphotograph of alumina nanoparticles with FIPC modified PEI coatings prepared in Example 2.

FIG. 9 is a fluorescence microphotograph photographed at a magnification of 1,000 times. The white parts show the fluorescence emitted by FITC. Since the particles are very fine, they appear dim overall. The whitest parts are the where the particles agglomerate.

(C) Particle Size Distribution

Figure 10:
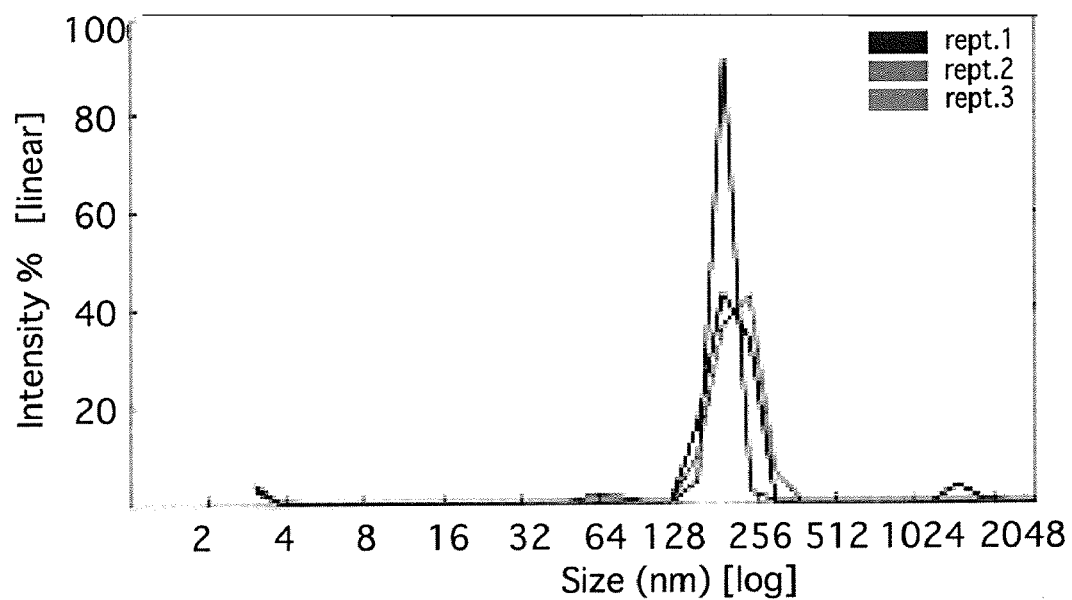
FIG. 10 is a graph of a particle size distribution of alumina nanoparticles with FIPC modified PEI coatings prepared in Example 2.

FIG. 10 is a graph of particle size distribution by dynamic scattering method of the FITC modified PEI covered alumina nanoparticles dispersion liquid. As can be understood from the graph of FIG. 10, the average particle size of the nanoparticles in the dispersion liquid was about 198 nm.

(D) Fluorescence Spectrum

Figure 11:
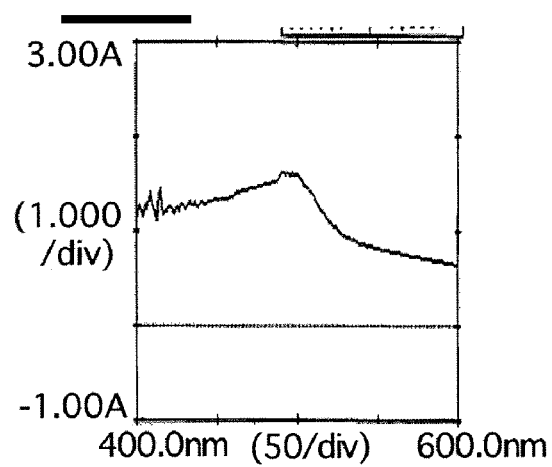
FIG. 11 is a fluorescence spectrum of alumina nanoparticles with FIPC modified PEI coatings prepared in Example 2.

FIG. 11 is an absorption spectrum of the FITC modified PEI covered alumina nanoparticles dispersion liquid. As can be understood from FIG. 11, the broad absorption spectrum having a peak top value at about 500 nm.

Example 3

Coating and Optical Characteristics of FITC Modified PEI Silica Nanoparticles

The FITC modified PEI coated silica nanoparticles are prepared by the process similar to Example 2, except that the silica nanoparticles (C.I. KASEI Ltd., JAPAN, NanoTek Powder; $SiO_2$) were used as starting particles, and various analysis were performed.

The results of various analysis of the FITC modified PEI covered silica obtained in Example 3 are as follows.

(A) Particle Shape

Figure 12:
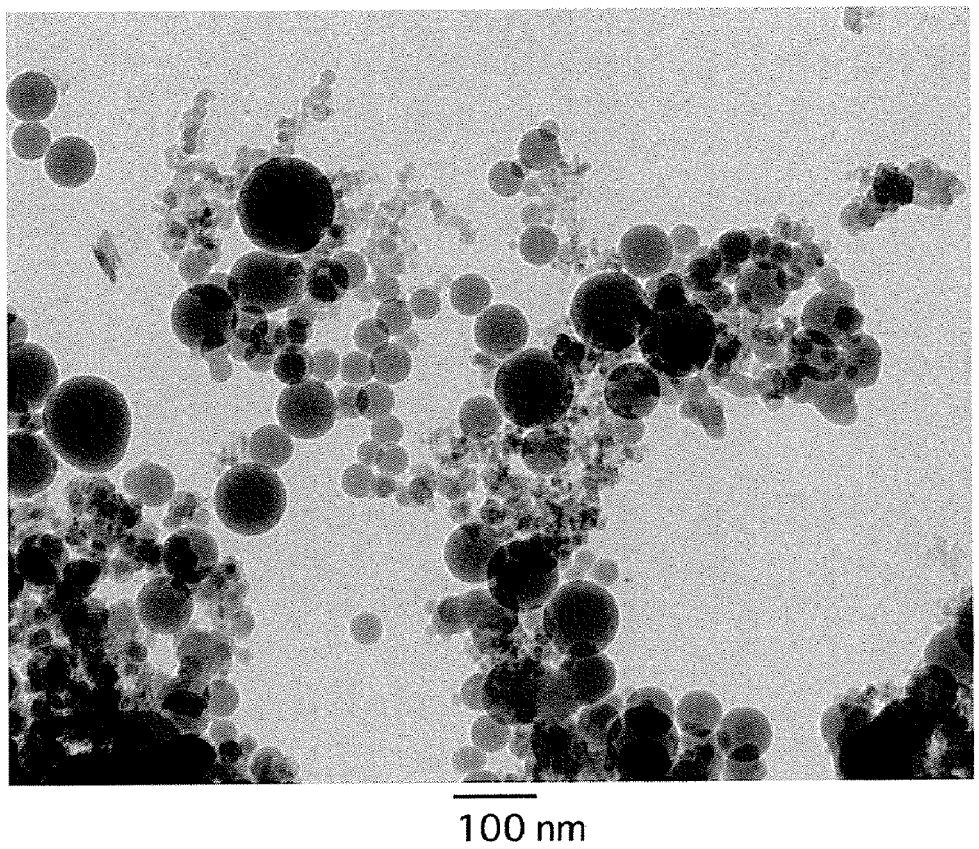
FIG. 12 is a transmission electron microphotograph of silica nanoparticles with FIPC modified PEI coatings prepared in Example 3.

FIG. 12 is a transmission electron microphotograph of the FITC modified PEI covered silica nanoparticles. As shown in this TEM photograph, the silica nanoparticles were spherical or oval-spherical with a size of 9 nm to 120 nm, and they are dispersed with several or more particles gathered together.

(B) Fluorescence Microphotograph

Figure 13:
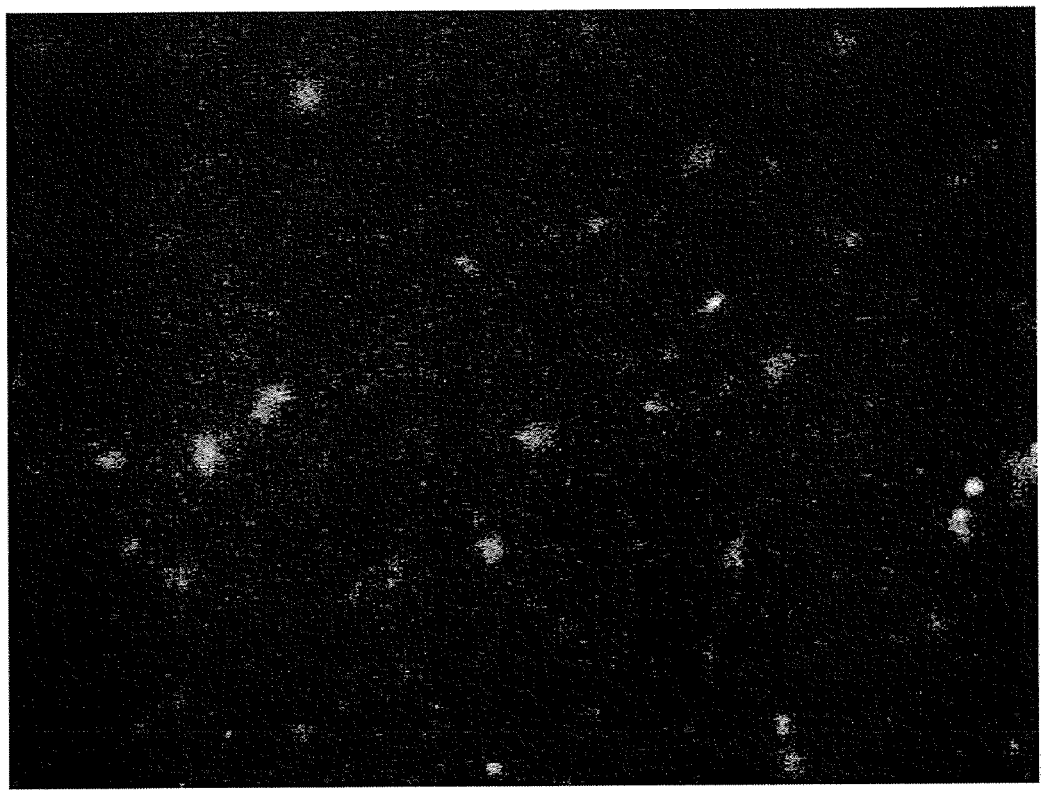
FIG. 13 is a fluorescence microphotograph of silica nanoparticles with FIPC modified PEI coatings prepared in Example 3.

FIG. 13 is a fluorescence microphotograph photographed at a magnification of 1,000 times. The white parts show the fluorescence emitted by FITC. Since the particles are very fine, they look dim overall. The whitest parts are where the particles agglomerate.

(C) Particle Size Distribution

Figure 14:
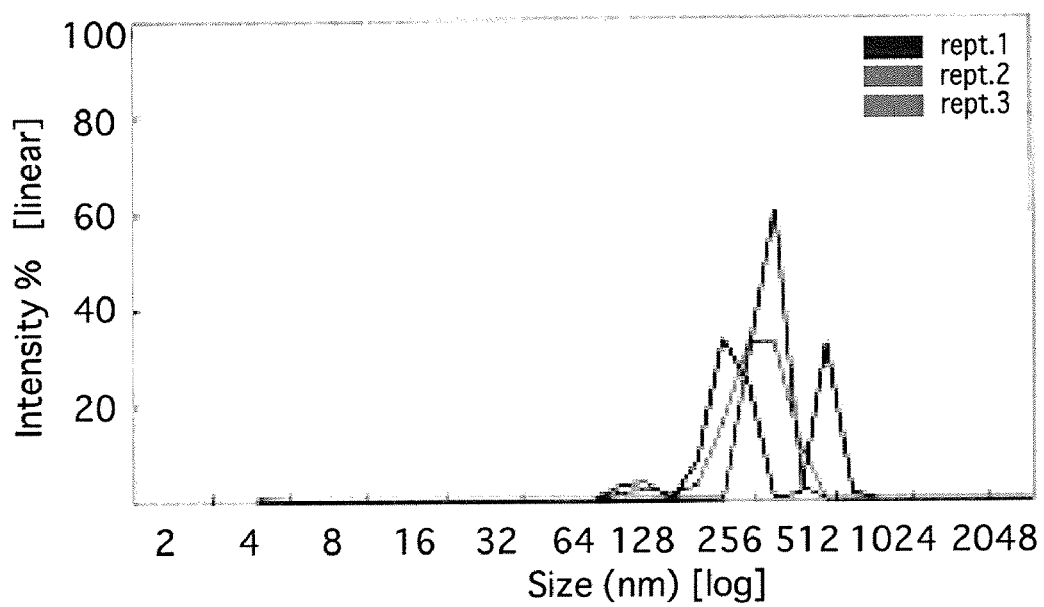
FIG. 14 is a graph of a particle size distribution of silica nanoparticles with FIPC modified PEI coatings prepared in Example 3.

FIG. 14 is a graph of a particle size distribution of the FITC modified PEI covered silica nanoparticles dispersion liquid by dynamic scattering method. As shown in FIG. 14, the average particle size of nanoparticles in the dispersion liquid was about 243 nm.

(D) Fluorescence Spectrum

Figure 15:
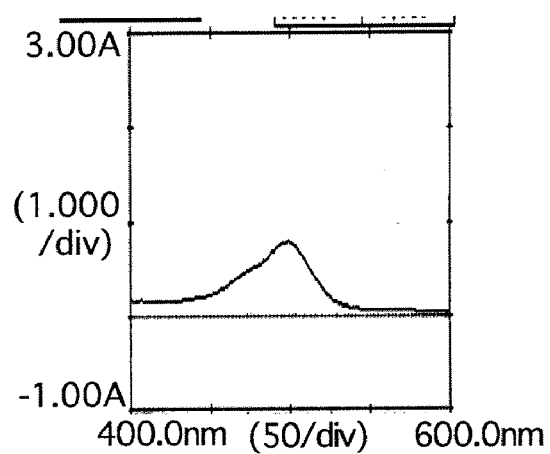
FIG. 15 is a fluorescence spectrum of silica nanoparticles with FIPC modified PEI coatings prepared in Example 3.

FIG. 15 is an absorption spectrum of the FITC modified PEI covered silica nanoparticles dispersion liquid. As can be

Example 4

Coating and Optical Characteristics of Rhodamine Modified PEI HA Nanoparticles (1) Preparation of Rhodamine Modified PEI Solution In order to prepare the rhodamine modified polyethylene imine solution, 7.5 mg of rhodamine (RhodamineB isothiocyanate) dissolved in 100 ml of distilled water and 100 mg of PEI (WAKO JUNYAKU Ltd., P-70; average molecular weight of 70,000) were mixed, and thereafter diluted with distilled water so as to obtain 75 mg/ml concentration of polyethylene imine.

(2) Preparation of Rhodamine Modified PEI Coated HA Nanoparticles

Rhodamine modified PEI coated HA nanoparticles were prepared by the process similar to Example 1, except that rhodamine modified PEI solution prepared according to above method (1) are used.

The results of various analysis of the rhodamine modified PEI covered HA nanoparticles obtained in Example 4 are as follows.

(A) Particle Shape

Figure 16:
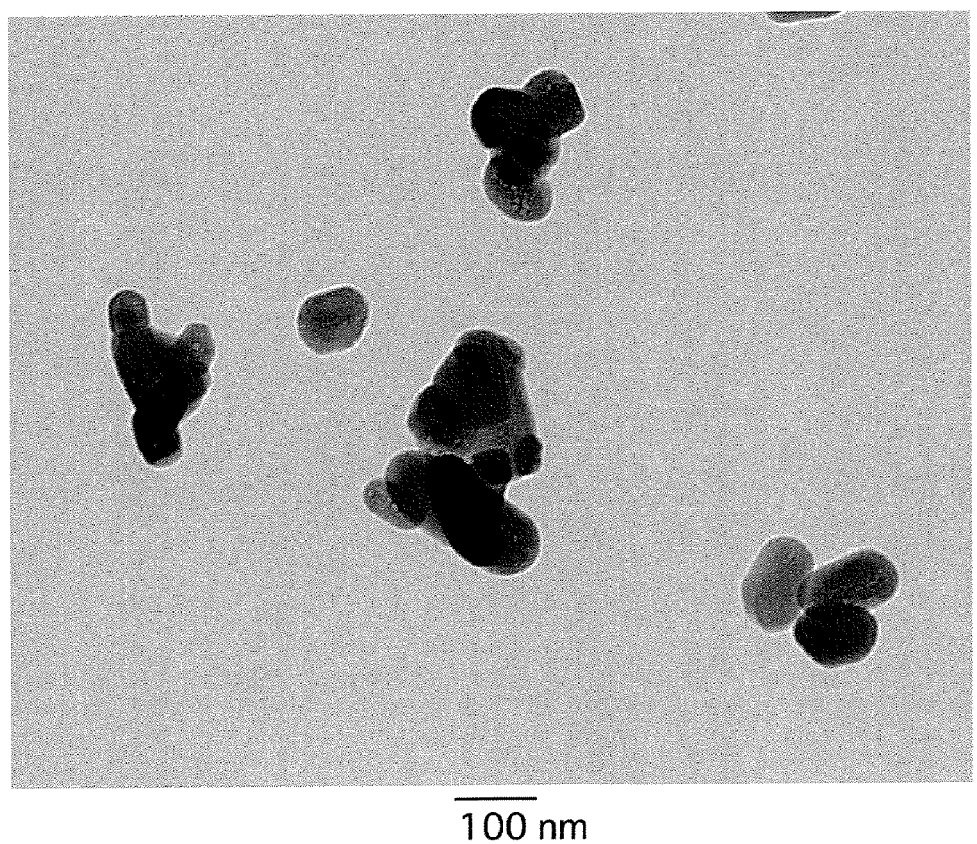
FIG. 16 is a transmission electron microphotograph of hydroxyapatite nanoparticles with rhodamine modified PEI coatings prepared in Example 4.

FIG. 16 is a transmission electron microphotograph of the rhodamine modified PEI covered HA nanoparticles. As shown in this TEM photograph, the HA nanoparticles were spherical or oval-spherical with a size of 50 nm to 180 nm and they are monodispersed or dispersed with several particles gathered together.

(B) Fluorescence Microphotograph

Figure 17A:
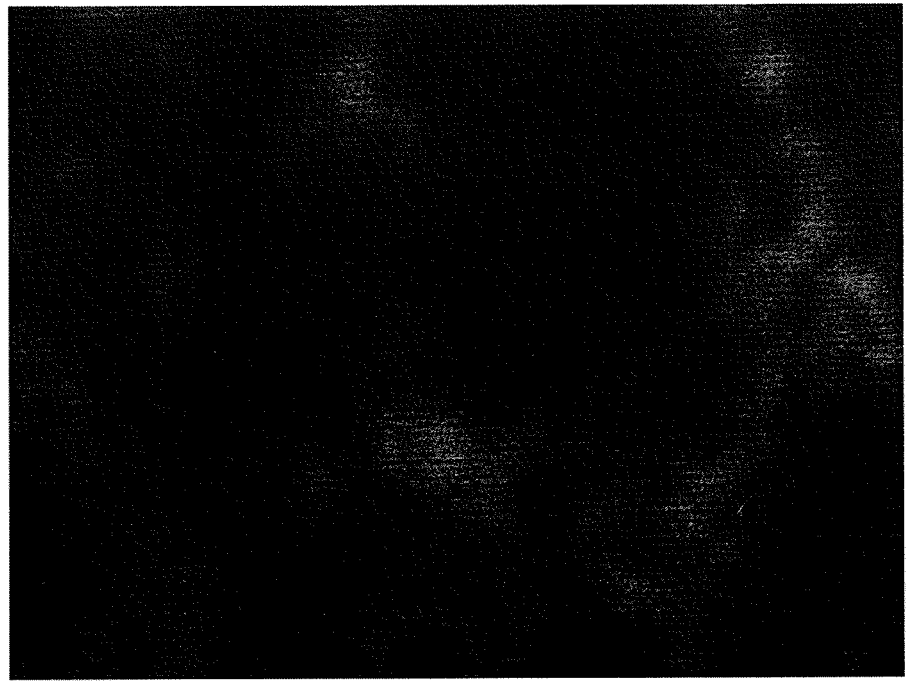
FIGS. 17A and 17B show a fluorescence microphotograph of hydroxyapatite nanoparticles with rhodamine modified PEI coatings prepared in Example 4.
Figure 17B:
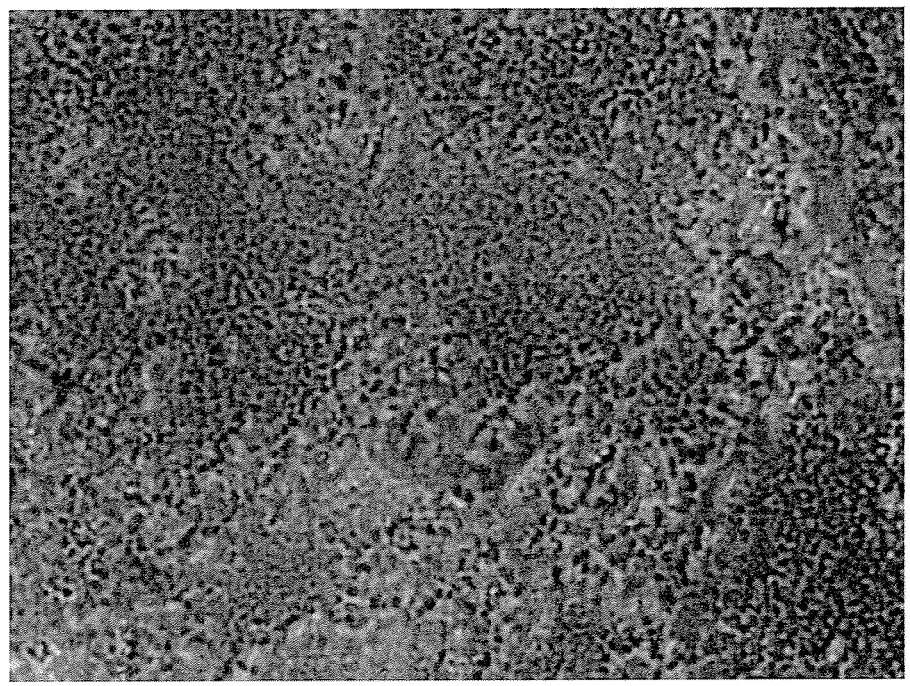

FIGS. 17A and 17B show fluorescence microphotographs of the rhodamine modified PEI covered HA nanoparticles. The photography magnification is 1,000 times and the same view is taken by phase difference observation (FIG. 17A) and is taken by fluorescence observation (FIG. 17B). Since the particles are extremely fine and fluorescence emitted from rhodamine is very strong, this photograph is taken at a short exposure time, and appears dim overall. The deep red parts in particular are where the particles agglomerate.

(C) Particle Size Distribution

Figure 18:
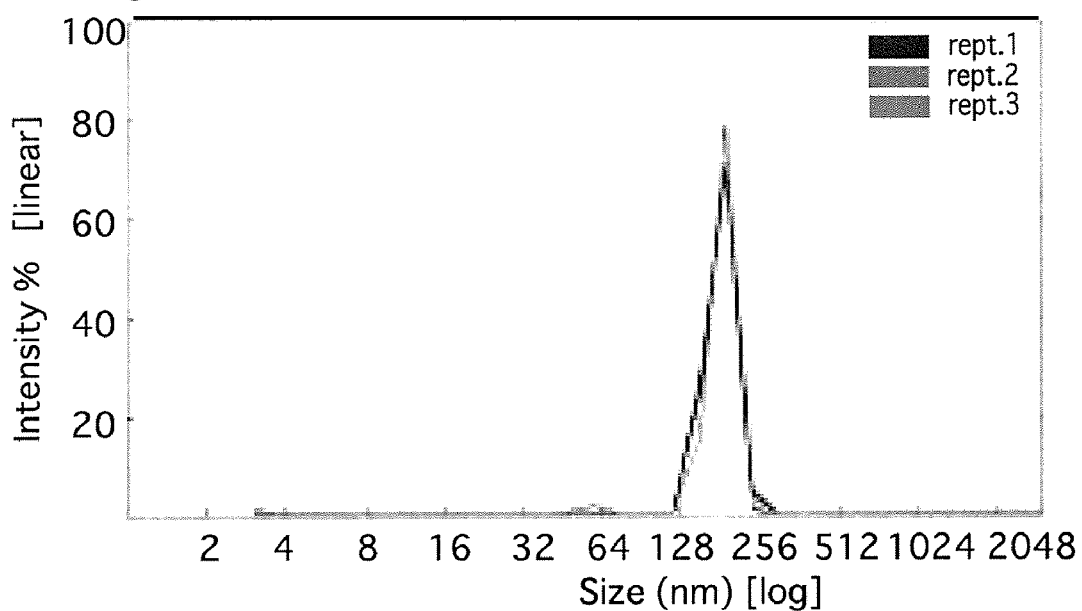
FIG. 18 is a graph of a particle size distribution of hydroxyapatite nanoparticles with rhodamine modified PEI coatings prepared in Example 4.

FIG. 18 is a graph of particle size distribution by dynamic scattering method of the rhodamine modified PEI covered HA nanoparticles dispersion liquid. As shown in FIG. 18, the average particle size of the nanoparticles in the dispersion liquid was about 181 nm.

Comparative Example 1

Optical Characteristics of FITC Only

The results of various analysis of the FITC solutions dissolved in distilled water, so that the FITC concentrations are same as Example 1 to 3 are as follows.

(A) Fluorescence Microphotograph

Figure 19A:
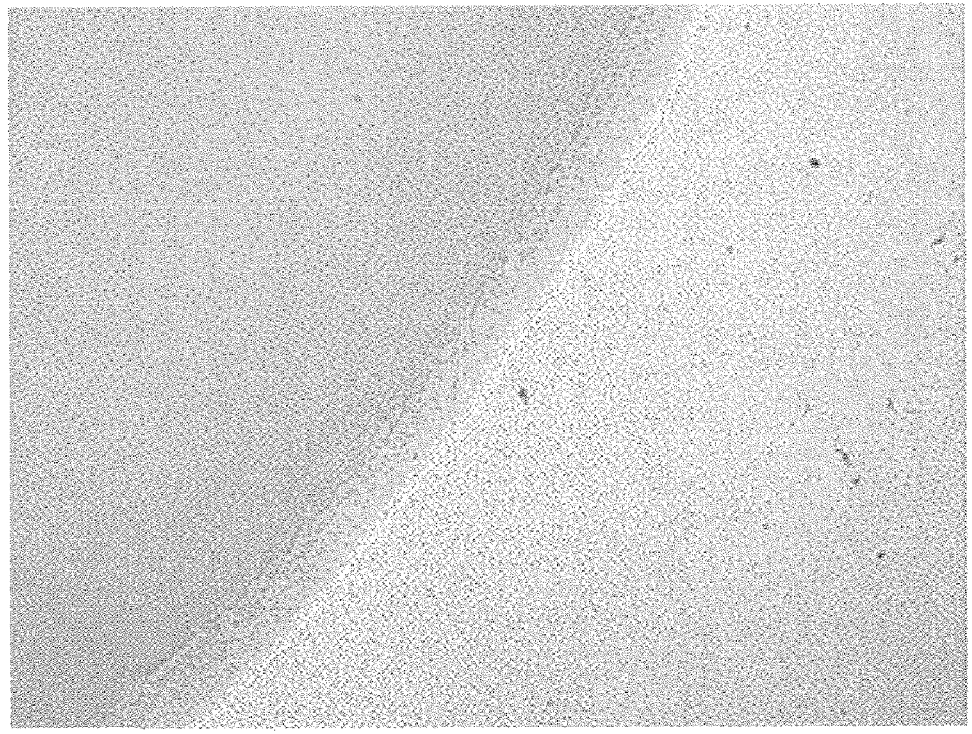
FIGS. 19A and 19B show a fluorescence microphotograph of FITC solution prepared in Comparative Example 1.
Figure 19B:
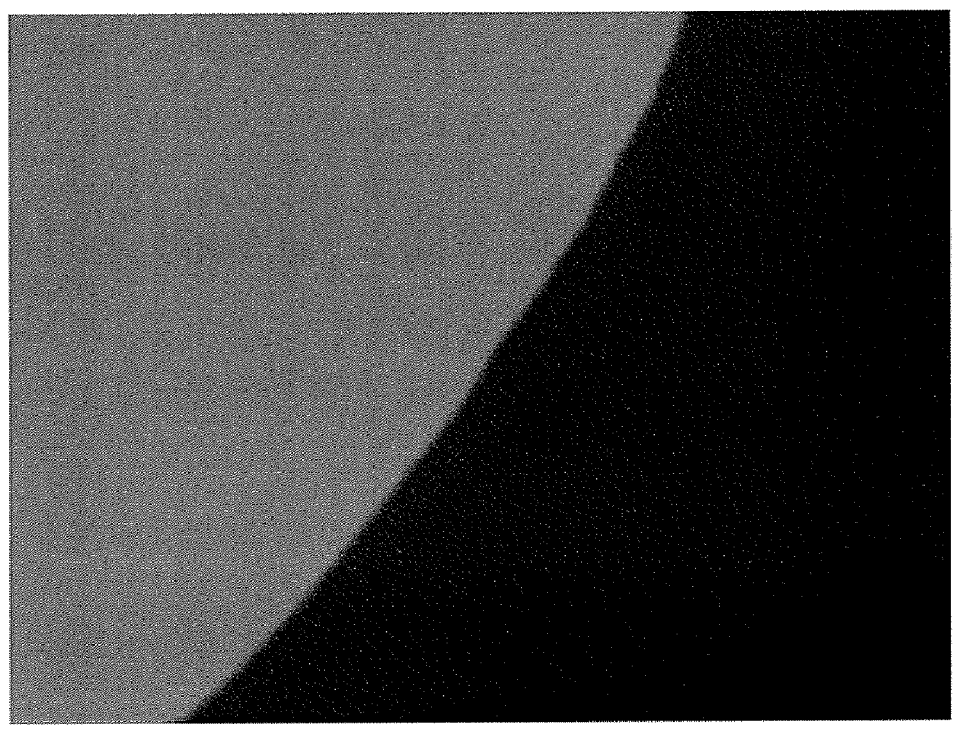

FIGS. 19A and 19B show a fluorescence microphotograph of FITC solution. The photography magnification is 100 times, and the same view is taken by phase difference observation (FIG. 17A) and by fluorescence observation (FIG. 17B). The solution was dripped only on the left-hand side in the photographs. Fluorescence was observed only on the left-hand side of FITC solution portion.

(D) Fluorescence Strength

Figure 20:
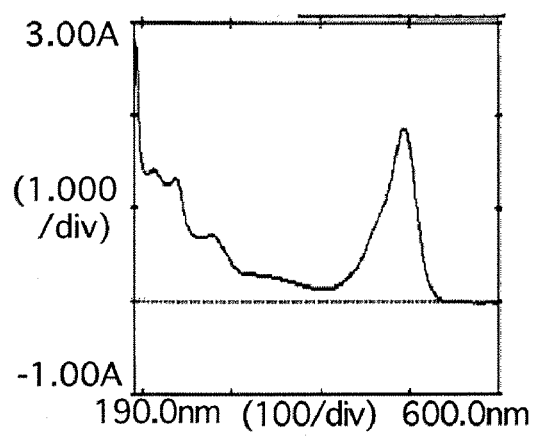
FIG. 20 is a fluorescence spectrum of FITC solution prepared in Comparative Example 1.

FIG. 20 is an absorption spectrum of FITC solution. As shown in FIG. 20, the broad absorption spectrum having a peak value at 200 nm and a peak top value at about 500 nm.

Comparative Example 2

Proof of Bonding PEI to FITC

Preparation of FITC Modified PEI Solution

In order to prepare FITC modified PEI solution, 5.4 mg of FITC dissolved in 100 ml of distilled water and 100 mg of PEI (WAKO JUNYAKU Ltd., P-70; average molecular weight of 70,000) were mixed, and thereafter diluted with distilled water so as to obtain 1.75 mg/ml concentration of polyethylene imine.

FITC modified PEI solution prepared was classified using gel filtration chromatography to remove excess FITC.

The results of various analysis of the FITC modified PEI solution obtained are as follows.

(B) Fluorescence Microphotograph

Figure 21A:
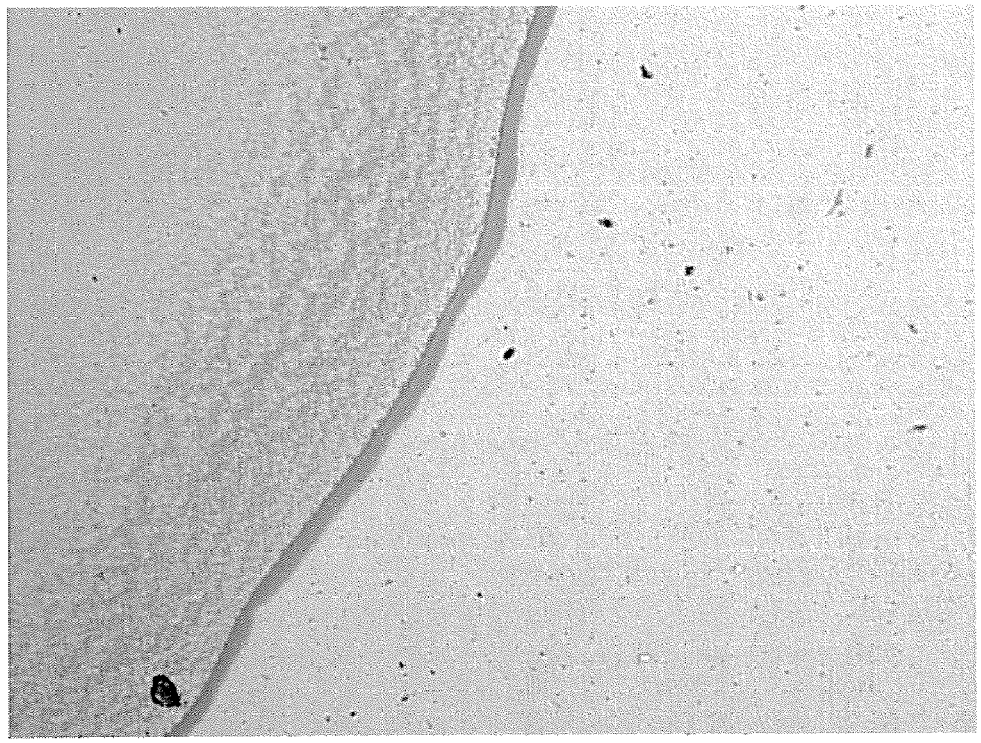
FIG. 21 is a fluorescence microphotograph of FITC modified PEI solution prepared in Comparative Example 2.
Figure 21B:
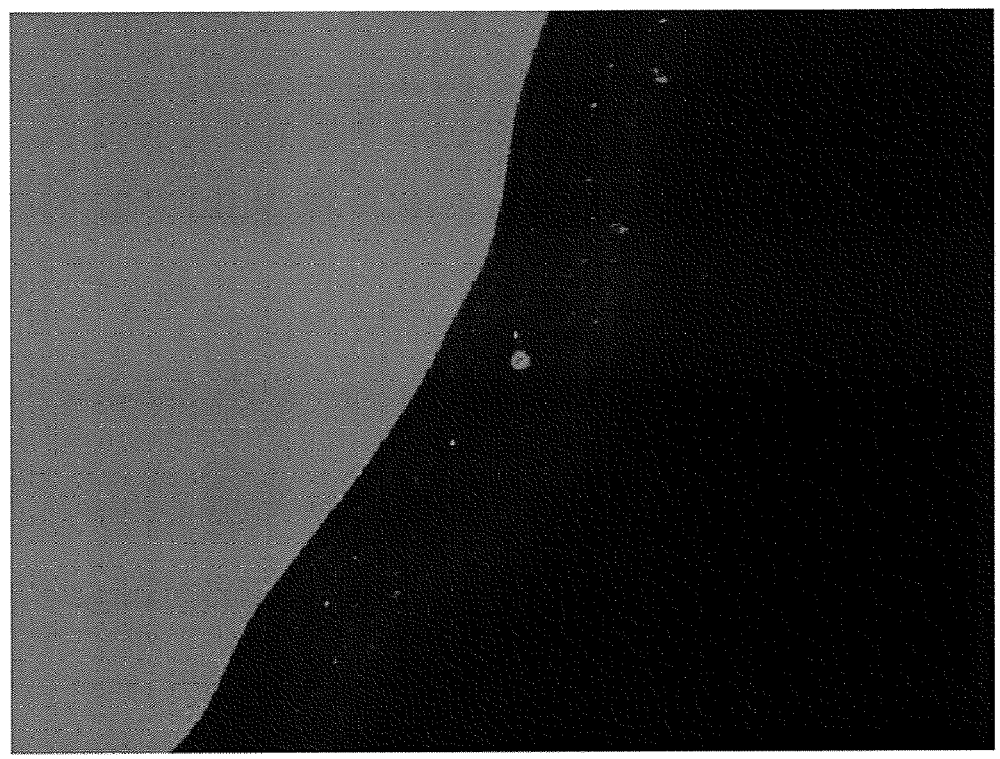

FIGS. 21A and 21B are fluorescence microphotographs of FITC modified PEI solution. The photographic magnification is 100 times and the same view is photographed by phase difference observation (21A) and by fluorescence observation (21B). The solution was dripped only on the left-hand side in the photographs. Fluorescence was observed only at FITC solution portion in the left-hand side.

(D) Fluorescence Strength

Figure 22:
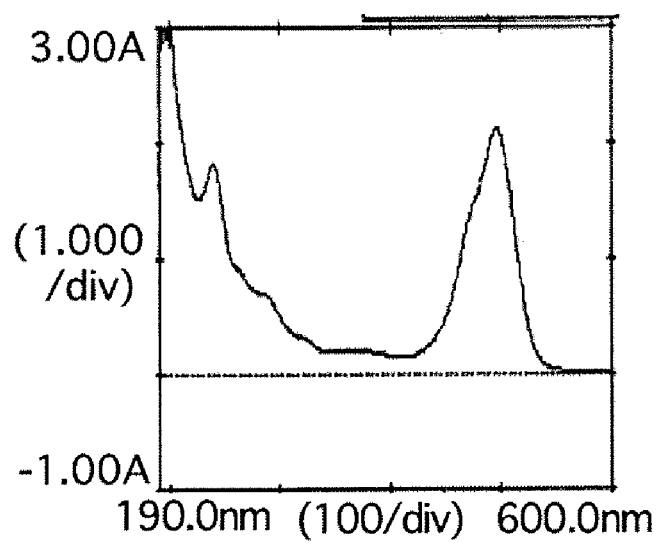
FIG. 22 is a fluorescence spectrum of FITC modified PEI solution prepared in Comparative Example 2.

FIG. 22 is an absorption spectrum of FITC modified PEI solution. The broad absorption peak having the peak at 200 nm and the peak top at about 500 nm is seen likewise Comparative example 1.

Although the invention has been described with reference to particular means, materials and embodiments, it is to be understood that the invention is not limited to the particulars disclosed and extends to all equivalents within the scope of the claims.

What is claimed is:

1. A modified calcium phosphate nanoparticle comprising:
a calcium phosphate nanoparticle, bonded to a polymer of ethylene imine through at least one amino group of the polymer of ethylene imine, wherein the polymer of ethylene imine is modified by at least one functional molecule
wherein the number average molecular weight of the polymer of ethylene imine is in the range of from 800 to 100,000.

2. The modified calcium phosphate nanoparticle according to claim 1, wherein said calcium phosphate compound comprises hydroxyapatite.

3. The modified calcium phosphate nanoparticle according to claim 1, wherein said functional molecules comprise organic coloring matters, inorganic coloring matters, fluorochromes or chemically identifiable molecules having chemiluminescent atomic groups.

4. The modified calcium phosphate nanoparticle according to claim 1, wherein the at least one functional molecule is selected from the group consisting of enzymes, antibodies, cell-irritating factors, collagen, virus envelope proteins, cell bonding ligands, colored proteins, fluoro-proteins, oligonucleotides, DNA, RNA, metal-storage proteins, monosaccharides, oligosaccharides or polysaccharides.

5. The modified calcium phosphate nanoparticle according to claim 1, wherein the number average molecular weight of the polymer of ethylene imine is in the range of from 70,000 to 100,000.

6. A method for producing the modified calcium phosphate nanoparticles according to claim 1, comprising:
   reacting the at least one functional molecules with a polymer of ethylene imine;
   mixing a solution containing the modified calcium phosphate nanoparticles with the modified ethylene imine polymer;
   centrifuging the mixture after ultrasonicating;
   collecting a supernatant of said mixture; and
   drying said supernatant.

7. The method for producing modified calcium phosphate nanoparticles according to claim 6, wherein said calcium phosphate compound comprises hydroxyapatite.

8. The method for producing modified calcium phosphate nanoparticles according to claim 6, wherein the solution of the mixing comprises water or an organic solvent.

9. The method for producing modified calcium phosphate nanoparticles according to claim 6, wherein said functional molecules comprise chemically identifiable molecules having organic coloring matters, inorganic coloring matters, fluorochrome or chemiluminescent atomic groups.

10. The method for producing modified calcium phosphate nanoparticles according to claim 6, wherein said functional molecules comprise molecules having a specific function and derived from a living body such as enzyme, antibody, cell-irritating factor, collagen, virus envelope protein, cell bonding ligand, colored protein, fluoro-protein, oligonucleotide, DNA, RNA, metal-storage protein, monosaccharides, oligosaccharides or polysaccharides.

* * * * *